United States Patent [19]

Kindl et al.

[11] Patent Number: 5,589,620
[45] Date of Patent: Dec. 31, 1996

[54] BIBENZYL SYNTHASE GENES

[75] Inventors: Helmut Kindl, Marburg; Rüdiger Hain, Langenfeld; Hans-Jörg Reif, Köln, all of Germany

[73] Assignee: Bayer Aktiengesellschaft, Leverkusen, Germany

[21] Appl. No.: 321,358

[22] Filed: Oct. 11, 1994

[30] Foreign Application Priority Data

Oct. 13, 1993 [DE] Germany ............ 43 34 791.6

[51] Int. Cl.$^6$ ............ A01H 5/00; A01H 5/10; C12N 15/29; C12N 15/82
[52] U.S. Cl. ............ 800/205; 800/250; 536/23.2; 536/23.6; 435/69.1; 435/172.3; 435/320.1; 435/252.3; 435/252.33; 435/240.4
[58] Field of Search ............ 435/69.1, 240.4, 435/252.3, 252.33, 320.1, 240.49, 172.3; 800/205, 255, 250; 536/23.6, 23.2

[56] References Cited

PUBLICATIONS

Hawley's Condensed Chemical Dictionary, 11th Edition, Van Nostrand Reinhold, New York, 1987, pp. 129, 143, 428, and 1094.
Hackh's Chemical Dictionary, 4th Edition, McGraw–Hill, New York 1969, p. 92.
Phytochemistry, Bd. 30, Nr. 2, 1991 Seiten 457–460, R. Gehlert, et al. Induced Formation of Dihydrophenathrenes and Bibenzyl Synthase Upon Destruction of Orchid Mycorrhiza.
Phytochemistry, Bd. 35, Nr. 1, Seiten 63–66, T. Reinecke, et al., Characterization of Bibenzyl Synthase Catalysing the Biosynthesis of Phytoalexins of Orchids.
Nature, Bd. 361, Jan. 14, 1993, Seiten 153–156, R. Hain, et al. Disease Resistance Results from Foreign Phytoalexin Expression in a Novel Plant.
Plant Molecular Biology, Bd. 15, 1990, Seiten 325–335, R. Hain, et al. Expression of a Stilbene Synthase Gene in Nicotiana Tabacum Results in Synthesis of the Phytoalexin Reservatrol.
Schroder et al (1988) Eur. J. Biochem 172: 161–169.

Primary Examiner—Douglas W. Robinson
Assistant Examiner—Elizabeth F. McElwain
Attorney, Agent, or Firm—Sprung Horn Kramer & Woods

[57] ABSTRACT

The present invention relates to novel genes, isolated from plants, for bibenzyl synthase and to their use for transforming vectors, host organisms and plants, as well as for producing plants which exhibit an increased resistance towards pests.

25 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 453 Base pairs
        ( B ) TYPE: Nucleic Acid
        ( C ) STRANDEDNESS: Single
        ( D ) TOPOLOGY: Linear ( i i ) MOLECULE TYPE: DNA (Genomic)

( i i i ) HYPOTHETICAL: No ( i i i ) ANTI-SENSE: No ( i x ) FEATURE:
        ( A ) NAME/KEY: CDS
        ( B ) LOCATION: complement (1..453)

( i x ) FEATURE:
        ( A ) NAME/KEY: CDS
        ( B ) LOCATION: 1..453

( x i ) SEQUENCE DESCRIPTION: SEQ ID NO: 1:

```
ATG  CCG  AGC  CTT  GAA  TCC  ATC  AAG  AAG  GCC  CCA  AGA  GCC  GAC  GGC  TTC        48
Met  Pro  Ser  Leu  Glu  Ser  Ile  Lys  Lys  Ala  Pro  Arg  Ala  Asp  Gly  Phe
 1                   5                   10                  15

GCC  TCC  ATT  TTG  GCC  ATC  GGG  AGG  GCG  AAC  CCA  GAC  AAT  ATT  ATT  GAA        96
Ala  Ser  Ile  Leu  Ala  Ile  Gly  Arg  Ala  Asn  Pro  Asp  Asn  Ile  Ile  Glu
                20                   25                  30

CAG  AGC  GCC  TAC  CCA  GAC  TTC  TAC  TTT  CGT  GTC  ACC  AAT  AGC  GAG  CAC       144
Gln  Ser  Ala  Tyr  Pro  Asp  Phe  Tyr  Phe  Arg  Val  Thr  Asn  Ser  Glu  His
           35                   40                   45

TTG  GTC  GAC  CTC  AAA  AAG  AAA  TTT  CAA  CGC  ATC  TGT  GAG  AAG  ACG  GCA       192
Leu  Val  Asp  Leu  Lys  Lys  Lys  Phe  Gln  Arg  Ile  Cys  Glu  Lys  Thr  Ala
      50                   55                   60

ATC  AGA  AAG  CGC  CAC  TTT  GTC  TGG  AAC  GAG  GAG  TTT  CTG  ACT  GCA  AAC       240
Ile  Arg  Lys  Arg  His  Phe  Val  Trp  Asn  Glu  Glu  Phe  Leu  Thr  Ala  Asn
 65                  70                   75                   80

CCT  TGC  TTC  AGC  ACA  TTC  ATG  GAC  AAA  TCT  TTA  AAC  GTA  AGG  CAA  GAG       288
Pro  Cys  Phe  Ser  Thr  Phe  Met  Asp  Lys  Ser  Leu  Asn  Val  Arg  Gln  Glu
                85                   90                   95

GTT  GCT  ATA  AGC  GAG  ATA  CCA  AAA  CTG  GGC  GCG  AAG  GCG  GCC  ACC  AAG       336
Val  Ala  Ile  Ser  Glu  Ile  Pro  Lys  Leu  Gly  Ala  Lys  Ala  Ala  Thr  Lys
          100                  105                  110

GCT  ATC  GAG  GAC  TGG  GGG  CAG  CCT  AAA  TCG  CGT  ATA  ACT  CAC  CTA  ATC       384
Ala  Ile  Glu  Asp  Trp  Gly  Gln  Pro  Lys  Ser  Arg  Ile  Thr  His  Leu  Ile
    115                    120                  125
```

```
TTC TGC ACC ACG AGC GGC ATG GAC TTA CCT GGT GCT GAT TAC CAG CTC      432
Phe Cys Thr Thr Ser Gly Met Asp Leu Pro Gly Ala Asp Tyr Gln Leu
    130             135                 140

ACC CAA ATC CCA ATG TTG AGC                                          453
Thr Gln Ile Pro Met Leu Ser
145             150
```

( 2 ) INFORMATION FOR SEQ ID NO: 2:

( i ) SEQUENCE CHARACTERISTICS:
        ( A ) LENGTH: 151 Amino acids
        ( B ) TYPE: Amino acid
        ( D ) TOPOLOGY: Linear ( i i ) MOLECULE TYPE: Protein ( x i ) SEQUENCE DESCRIPTION: SEQ ID NO: 2:

```
Met Pro Ser Leu Glu Ser Ile Lys Lys Ala Pro Arg Ala Asp Gly Phe
  1           5               10                  15

Ala Ser Ile Leu Ala Ile Gly Arg Ala Asn Pro Asp Asn Ile Ile Glu
             20              25                  30

Gln Ser Ala Tyr Pro Asp Phe Tyr Phe Arg Val Thr Asn Ser Glu His
         35              40                  45

Leu Val Asp Leu Lys Lys Lys Phe Gln Arg Ile Cys Glu Lys Thr Ala
     50              55                  60

Ile Arg Lys Arg His Phe Val Trp Asn Glu Glu Phe Leu Thr Ala Asn
 65              70              75                          80

Pro Cys Phe Ser Thr Phe Met Asp Lys Ser Leu Asn Val Arg Gln Glu
                 85                  90                      95

Val Ala Ile Ser Glu Ile Pro Lys Leu Gly Ala Lys Ala Ala Thr Lys
             100             105                 110

Ala Ile Glu Asp Trp Gly Gln Pro Lys Ser Arg Ile Thr His Leu Ile
         115                 120                 125

Phe Cys Thr Thr Ser Gly Met Asp Leu Pro Gly Ala Asp Tyr Gln Leu
    130             135                 140

Thr Gln Ile Pro Met Leu Ser
145             150
```

BIBENZYL SYNTHASE GENES

BACKGROUND OF THE INVENTION

The present invention relates to novel genes, isolated from plants, for bibenzyl synthase, and to their use for transforming vectors, host organisms and plants as well as for producing plants which exhibit an increased resistance towards pests.

Phenolic constituents, in particular 1-(3,5-dihydroxyphenyl)-2-(3-hydroxyphenyl)-ethane, which occur in orchids and have a toxic effect on pests, in particular fungi, bacteria and insects, and are thus suitable for protecting against these pests, are designated bibenzyls. The ability of orchids to synthesize these substances is considered to be an important defence mechanism. Plants of commercial importance are not known to have the ability to form bibenzyls or to produce them in a quantity which confers adequate resistance to pests.

It is known from EP-A 0 309 862 and EP-A 0 464 461 to use stilbene synthase genes for producing plants having an increased resistance to pests. These publications describe resveratrol synthase genes from groundnut plants and vines, in particular.

SUMMARY OF THE INVENTION

Novel genes for synthesizing bibenzyl ("bibenzyl synthase genes") have now been found, which genes can be incorporated into the hereditary material (the genome) of plants which either do not produce any bibenzyls or only produce bibenzyls in insufficient quantity, thereby giving rise to increased resistance in these plants to pests. The term bibenzyls means phenolic bibenzyls, preferably 1-(3,5-dihydroxyphenyl)-2-(3-hydroxyphenyl)ethane.

Surprisingly, the corresponding transgenic plants express bibenzyls and exhibit favorable resistances to pests without the occurrence of any effects which are disadvantageous to the plants.

A bibenzyl synthase gene is understood to mean any nucleic acid (DNA) which, after its transcription into RNA and translation into protein, brings about the formation of an enzyme which possesses the properties of a bibenzyl synthase (consequently effecting bibenzyl formation), with this nucleic acid being isolated from its natural environment or integrated into a vector, or being contained in a procaryotic or a eucaryotic DNA as "foreign" DNA or as "additional" DNA.

Bibenzyl synthase genes are also understood to mean those bibenzyl synthase genes which, at their beginning and/or end, contain further DNA sequences which either do not impede the function of the genes or only do so to an insignificant extent. These DNA sequences, also termed "gene units", arise, for example, as a result of excision with restriction enzymes when no cleavage sites for customary restriction enzymes are present exactly at the beginning and at the end of the gene. The bibenzyl synthase genes and the gene units can also carry at their ends those DNA sequences which are in each case designed for handling the genes (e.g. "linkers").

The bibenzyl synthase genes (or the gene units) can be present in the form in which they are contained in the genome of plants ("genomic" form, including sequences (such as introns) which do not code for bibenzyl synthase and/or do not have a regulatory effect) or in a form which corresponds to the cDNA (copy DNA), which can be obtained by way of mRNA using reverse transcriptase/polymerase (and does not contain any introns). The bibenzyl synthase genes can also be present in a form which is partially or completely synthetic. Synthetic genes are also understood to be those which arise as a result of the novel splicing of parts of corresponding natural genes.

Segments of the DNA of the bibenzyl synthase genes (or the gene units) according to the invention can be replaced by other DNA segments or DNA's which essentially have the same effect, as long as the genes still bring about the formation of bibenzyl. The genes or gene parts according to the invention also include those in which DNA variations are present due to the degeneracy of the genetic code.

In the present connection, "foreign" DNA is understood to mean that DNA which is not naturally present in a particular prokaryotic or eukaryotic genome, but is only taken up into this genome as a result of human intervention (transformation). "Additional" DNA is intended to mean that DNA which, while being present naturally in the relevant prokaryotic or eukaryotic genome, is taken up into this genome in additional amount as a result of human intervention (transformation). Depending on the requirement and on the nature of the particular case, the "foreign" DNA or "additional" DNA can be incorporated in one or more copies.

Bibenzyl synthase, which is formed in plants or plant cells with the involvement of the bibenzyl synthase genes (or the gene units) according to the invention, denotes each enzyme which acts as a bibenzyl synthase, that is, produces one or more bibenzyls, and increases the resistance of plants towards pests.

The preferred bibenzyl synthase genes according to the invention are characterized in that they hybridize to the cDNA sequence, or its parts, contained in the plasmid pin p8.1.1 or to the cDNA sequence according to SEQ ID NO: 1, or its parts, and code for bibenzyl synthase.

Bibenzyl synthase genes which are preferred according to the invention are the bibenzyl synthase genes which are present in orchids, particularly preferably in Phalaenopsis spp., *Bletilla striata* or *Epipactis palustris*, and can be isolated therefrom. The The bibenzyl synthase gene whose partial sequence is present, in the form of the cDNA, on the plasmid p8.1.1 (which is described in detail below), and the DNA sequences which essentially have the same effect, are very particularly preferred as bibenzyl synthase genes according to the invention. The cDNA on the plasmid p8.1.1. corresponds to the structural gene coding for bibenzyl synthase. The cDNA on plasmid p8.1.1 can thus be used directly as a bibenzyl synthase structural gene.

The cDNA contained on the plasmid was isolated from Phalaenopsis. The cDNA consists of a sequence of approximately 1,600 base pairs in length. A partial sequence of 453 base pairs is contained in the sequence listing SEQ ID NO: 1. The protein sequence deriving therefrom is contained in SEQ ID NO: 2.

It has been found that the bibenzyl synthase genes present in orchids (in particular in Phalaenopsis spp., *Bletilla striata* and *Epipactis palustris*) exhibit DNA sequence homology over long stretches. Owing to the sequence homology, the bibenzyl synthase genes according to the invention can therefore be isolated in a simple manner from plants by the customary and known methods of molecular biology using the cDNA, or its parts, contained on plasmid p8.1.1, or the sequence information in accordance with SEQ ID NO: 1.

Practically all orchid species, preferably Phalaenopsis spp., *Bletilla striata* and *Epipactis palustris*, are suitable for use as plants from which bibenzyl synthase genes according to the invention can be isolated. As already mentioned, bibenzyl synthase genes according to the invention, or their coding regions, are preferred which hybridize to the cDNA which is present on the plasmid p8.1.1. The gene, or the coding region of the gene, can be obtained in a customary manner using the cDNA. In accordance with the invention, the cDNA sequence contained on plasmid p8.1.1, or a corresponding DNA sequence which contains the sequence of this cDNA sequence, is particularly preferred as the coding region (or structural gene).

The *Escherichia coli* strain *E. coli* p8.1.1 contains plasmid p8.1.1. This strain has been deposited with the Deutsche Sammlung von Mikroorganismen (DSM) (German Collection of Microorganisms), Mascheroder Weg 1b, D-38124 Braunschweig, Federal Republic of Germany, in conformity with the stipulations of the Budapest treaty on the international recognition of the deposition of microorganisms for the purposes of patent processes (deposition date: 27 th Sep. 1993). It was given the deposition number DSM 8580.

This strain, and its mutants, are likewise a part of the present invention. The plasmid p8.1.1 deposited in this host can readily be isolated in the required quantities in a conventional manner by replicating the strain and subsequently isolating the plasmid.

Functionally complete genes, such as the bibenzyl synthase genes according to the invention, consist of a regulatory part (in particular a promoter) and the structural gene which codes for the protein bibenzyl synthase.

Both the gene parts can be used independently of each other. Thus, it is possible to locate another DNA sequence (differing from the bibenzyl synthase gene), which is to be expressed following incorporation into the plant genome, downstream of the regulatory part. Since only relatively few isolated promoters are known which are able to display their effect in plants or plant cells, the promoters of the bibenzyl synthase genes, which are likewise constituents of the present invention, represent valuable aids in the production of transformed plants or plant cells.

It is likewise possible to locate a "foreign" regulatory part upstream of the bibenzyl synthase structural genes. In this connection, the stilbene synthase promoters according to EP-A 0 309 862 and EP-A 0 464 461 can be employed with particular advantage. This could, for example, be advantageous when only certain regulatory genes (e.g. endogenous to the plant) are able to be sufficiently active in particular plants. The bibenzyl synthase structural genes, particularly, as well, the structural genes which correspond to the cDNA of plasmid p8.1.1 or which contain this sequence thus represent valuable units which can be independently employed, and are, as already explained, likewise part of the present invention. The bibenzyl synthase genes according to the invention can be separated by the customary methods into the regulatory parts and the structural genes. It is also possible to combine parts of different naturally occurring bibenzyl synthase genes to make novel, functional "synthetic" genes. The complete, natural bibenzyl synthase genes according to the invention (or the gene units) are preferably used.

It is possible, using the customary methods, to incorporate the bibenzyl synthase genes (or the gene units), or their parts, once or more than once (e.g. tandem arrangement), preferably once, into arbitrarily selected procaryotic (preferably bacterial) or eucaryotic (preferably plant) DNA as "foreign" or "additional" DNA. Thus, for example, the protein-encoding DNA can be provided with regulatory sequences and incorporated into plants. The recombinant DNA "modified" in this way, which can be used, for example, for transforming plants or plant cells and, following transformation, is contained in plants or plant cells, is a constituent of the present invention.

The bibenzyl synthase genes (or the gene units) and/or their parts, as well as the recombinant DNA, can be contained, as "foreign" or "additional" DNA, in vectors (in particular plasmids, cosmids or phages), in transformed microorganisms (preferably bacteria, in particular Gram-negative bacteria such as *E. coli*) and in transformed plant cells and plants or in their DNA. Such vectors, transformed microorganisms (which can also harbor these vectors) and the transformed plant cells and plants and their DNA represent constituents of the present invention.

As already indicated, the bibenzyl synthase genes (or the gene units) are, in accordance with the invention, incorporated once or more than once (at the same or different sites in the genome) into the natural plant genome, it also being possible to combine different genes with each other. In the case of plants which are already able to synthesize bibenzyl synthase (orchids), the incorporation of one or more bibenzyl synthase genes according to the invention can lead to substantially improved resistances. In the case of plants which do not contain any bibenzyl synthase genes, an increased resistance to pests is likewise achieved by incorporating such genes. If appropriate, only the structural genes according to the invention are used with a regulatory DNA element that might have been isolated from another plant or from the particular plant in question being located upstream of them.

The increased resistance of the transformed plant cells and plants according to the invention is of importance for agriculture and forestry, for the cultivation of ornamental plants, the cultivation of medicinal plants and for plant breeding. It is also advantageous when cultivating plant cells, e.g. in order to obtain pharmaceutically utilizable substances, to have available plant cells which exhibit increased resistances to infestation with microbial pests, in particular fungi.

The present invention consequently also relates to a process for preparing transgenic plant cells (including protoplasts) and plants (including plant parts and seeds) possessing an increased resistance to pests, which process is characterized in that (a) one or more bibenzyl synthase genes (or gene units) and/or parts of the bibenzyl synthase genes (or of the gene units) and/or recombinant DNA according to the invention, which contains DNA sequences which code for bibenzyl synthase, are inserted into the genome of plant cells (including protoplasts) and, where appropriate, (b) complete transformed plants are regenerated from the transformed plant cells (including protoplasts) and, where appropriate, replicated, and, where appropriate, (c) the desired plant parts (including seeds) are isolated from the transgenic plants, thus obtained, of the parental generation or of further generations obtained therefrom.

The process steps (a), (b) and (c) can be carried out in a customary manner in accordance with known processes and methods.

Transgenic plant cells (including protoplasts) and plants (including plant parts and seeds) which contain one or more bibenzyl synthase genes (or gene units) and/or parts of the bibenzyl synthase genes (or of the gene units) as "foreign"

or "additional" DNA, and those transformed plant cells and plants which are obtainable in accordance with the above processes, are likewise included in the present invention.

The following are also parts of the present invention:

(a) The use of the bibenzyl synthase genes (or of the gene units) and/or of their parts and/or of the recombinant DNA according to the invention and/or of the recombinant vectors according to the invention and/or of the transformed microorganisms according to the invention for transforming plant cells (including protoplasts) and plants (including plant parts and seeds), (b) the use of the transgenic plant cells (including protoplasts) and plants (including plant parts and seeds) according to the invention for producing replication material and for producing new plants and their replication material, (c) the use of the bibenzyl synthase genes (or of the gene units) according to the invention, and/or of their parts and/or of the recombinant DNA according to the invention, for controlling pests, and (d) the use of the cDNA contained on plasmid p8.1.1, or of its parts, and of the DNA sequences corresponding to the sequence information in accordance with sequence listing SEQ ID NO: 1, for isolating bibenzyl synthase genes, or their parts, from plants, and for determining bibenzyl synthase genes in plants, and (generally) in the production of transgenic plant cells (including protoplasts) and plants (including plant parts and seeds), as well as the use of the protein sequence (bibenzyl synthase) encoded by the structural gene of p8.1.1, and of the protein in accordance with SEQ ID NO:2, in the isolation and detection of the bibenzyl synthase genes (e.g. by means of the customary antibody technique). The bibenzyl synthase encoded by the bibenzyl synthase genes according to the invention (in particular by the structural gene of p8.1.1), as well as the protein in accordance with SEQ ID NO:2, are likewise included in the present invention.

A number of different methods are available for inserting the bibenzyl synthase genes or the gene units or their parts, as "foreign" or "additional" DNA, into the genetic material of plants or plant cells. The gene transfer can be effected by the common, generally known, methods, the person skilled in the art being able, without difficulty, to ascertain the method which is suitable on each occasion.

The Ti plasmid from Agrobacterium tumefaciens is available as a particularly favorable, and widely applicable, vector for transferring foreign DNA into genomes of dicotyledonous and monocotyledonous plants. The genetic material which codes for bibenzyl synthase is inserted, together with regulatory DNA sequences, into the T DNA of suitable Ti plasmids (e.g. Zambryski et al., 1983) and transferred by infection of the plant, infection of plant parts or plant tissues, such as, for example, of leaf disks, stems, hypocotyls, cotyledons, meristems and tissues derived therefrom, such as, for example, secondary embryos and calluses, or by coculturing protoplasts with Agrobacterium tumefaciens.

An alternative is to incubate purified DNA containing the desired gene in plant protoplasts (e.g. Hain et al., 1985; Krens et al., 1982; Paszkowski et al., 1984) in the presence of polycations or calcium salts and polyethylene glycol.

The uptake of the DNA can also additionally be encouraged by using an electrical field (electroporation) (e.g. Fromm et al., 1986).

The DNA can also, in a known manner, be introduced by way of plant pollen, with pollen, or other plant parts, being "bombarded" with physically accelerated particles which carry the DNA (cf. EP-A 0 270 356).

The plants are regenerated in a known manner using suitable nutrient media (e.g. Nagy and Maliga 1976). In a preferred embodiment of the process according to the invention (in accordance with the method from EP-A 116 718), the genes or gene units according to the invention are cloned, in isolated form, into a suitable intermediate E. coli vector, e.g. pGV700 or pGV710 (cf. EP-A 116 718), or, preferably, derivatives thereof, which additionally contain a reporter gene such as, for example, nptII (Herrera-Estrella et al. 1983) or hpt (Van den Elzen et al 1986).

The plasmid constructed in this way is transferred using customary methods (e.g. Van Haute et al. 1983) into Agrobacterium tumefaciens which harbors, for example, pGV 3850 or derivatives thereof (Zambryski et al. 1983). Alternatively, the bibenzyl synthase gene unit can be cloned in a binary vector, e.g. pCV001 or pCV002 (e.g. Koncz and Schell 1986) and then transferred, as described above, into a suitable Agrobacterium strain (Koncz and Schell 1986). The resulting Agrobacterium strain, which contains the bibenzyl synthase genes or gene units in a form which is transferrable to plants, is subsequently used for transforming plants.

In a further preferred embodiment, the isolated bibenzyl synthase gene units, where appropriate together with another plasmid which contains a reporter gene for plant cells, e.g. for kanamycin resistance (e.g. Herrera-Estrella et al. 1983) or a hygromycin resistance (van den Elzen, 1986), preferably pLGV neo 2103 (Hain et al. 1985), pMON 129 (Fraley R. T. et al., Proc. National Acad. Sci. USA 80, 4803 (1983)), pAK 1003, pAK 2004 (Velten J. et al., EMBO Journ. Vol. 3, 2723 (1984)) or pGSST neo 3 (pGSST3) (EP-A-189 707), are transferred in a customary manner to plant protoplasts by means of direct gene transfer (e.g. Hain et al 1985). For this, the plasmid(s) can be present in circular form, but is/are preferably present in linear form. When a plasmid containing a reporter gene is used, kanamycin-resistant protoplasts are then screened for the expression of bibenzyl synthase. In the alternative case (without reporter gene), the resulting calluses are screened for the expression of the bibenzyl synthase gene(s) (screening using customary methods).

Transformed (transgenic) plants or plant cells are produced by the known methods, e.g. by transforming leaf disks (e.g. Horsch et al. 1985), by coculturing regenerating plant protoplasts or cell cultures with Agrobacterium tumefaciens (e.g. Marton et al. 1979, Hain et al. 1985), or by directly transfecting with DNA. Transformed plants which result are detected either by selecting for the expression of the reporter gene, e.g. by the phosphorylation of kanamycin sulfate in vitro (Reiss et al. 1984; Schreier et al. 1985), or by expression of nopaline synthase (in accordance with Aerts et al. 1983) or bibenzyl synthase using Northern blot analysis and Western blot analysis. Bibenzyl synthase and the bibenzyls can also be detected, in a known manner, in transformed plants using specific antibodies. Bibenzyl synthase can also be detected using an enzyme activity test.

The transformed plant cells are cultivated, and regenerated into complete plants, in accordance with the common, generally known, methods using the nutrient media which are suitable on each occasion.

Both the transformed plant cells and the transformed plants which contain the bibenzyl synthase genes (or the gene units) according to the invention, and which are constituents of the present invention, exhibit substantially greater resistance to pests, in particular to phytopathogenic fungi.

In connection with the present invention, the expression "plants" denotes both complete plants and plant parts, such as leaves, seeds, tubers, cuttings, etc. "Plant cells" include protoplasts, cell lines, plant calluses, etc. "Replication material" denotes plants and plant cells which can be used for replicating the transformed plants and plant cells, and is, consequently, likewise a part of the present invention.

In the present context, the expression "DNA sequences having essentially the same effect" denotes that the invention also embraces those modifications in which the function of the bibenzyl synthase genes and of their parts is not impaired in such a way that bibenzyl synthase is no longer formed or that the regulatory gene part is not longer active. Relevant modifications can be effected by replacing, adding and/or removing DNA segments, individual codons and/or individual nucleic acids. They can also be present in view of the degeneracy of the genetic code.

In the case of the microorganisms which can be used in accordance with the invention, "mutants" denotes those modified microorganisms which also exhibit the features which are essential for implementing the invention, and, in particular, harbor the plasmid p8.1.1.

The plants on which resistance, or an increased resistance, towards pests can be conferred by the incorporation (transformation) of the bibenzyl synthase genes (or the gene units) according to the invention include practically all plants apart from orchids, in which bibenzyl synthase genes occur naturally. There is a particular need for producing resistance, naturally, in the case of the cultivated plants, such as forest plants, e.g. spruce, fir, douglas fir, pine, larch, beech and oak, as well as plants supplying nutrients and raw materials, e.g. cereals (in particular wheat, rye, barley, oats, millet, rice and corn), potatoes, leguminosi (such as pulses and, in particular, alfalfa and soya beans), vegetables (in particular cabbage species and tomatoes), fruit (in particular apples, pears, cherries, grapes, citrus fruit, pineapples and bananas), oil palms, tea, cocoa and coffee bushes, tobacco, sisal and cotton, as well as in the case of medicinal plants, such as Rauwolfia and Digitalis. Potatoes, tomatoes and leguminosi may be mentioned with particular preference. Preferably, the bibenzyl synthase genes according to the invention are incorporated, as "foreign" DNA, into the genome of plants.

Animal pests, such as insects, mites and nematodes, and microbial pests, such as phytopathogenic fungi, bacteria and viruses, may be mentioned as pests against which resistances, or increased resistances, can be achieved with the aid of the bibenzyl synthase genes according to the invention. Microbial pests, in particular phytopathogenic fungi, are particularly emphasized.

The pernicious insects particularly include insects of the orders:

Orthoptera, Dermaptera, Isoptera, Thysanoptera, Heteroptera, Homoptera, Lepidoptera, Coleoptera, Hymenoptera and Diptera.

The pernicious mites particularly include:

Tarsonemus spp., Panonychus spp. and Tetranychus spp.

The pernicious nematodes particularly include:

Pratylenchus spp., Heterodera spp. and Meloidogyne spp.

The microbial pests particularly include the phytopathogenic fungi:

Plasmodiophoromycetes, Oomycetes, Chytridiomycetes, Zygomycetes, Ascomycetes, Basidiomycetes, Deuteromycetes.

The phytopathogenic bacteria particularly include the Pseudomonadaceae, Rhizobiaceae, Enterobacteriaceae, Corynebacteriaceae and Streptomycetaceae.

The viral diseases particularly include mosaic, dwarfing and yellowing virus diseases.

Some causative agents of viral, fungal and bacterial diseases, which come within the above-listed categories and which may be mentioned by way of example, but not by way of delimitation, are:

Barley yellow dwarf virus (BYDV), potato virus Y (PVY), cucumber mosaic virus (CMV), watermelon mosaic virus (WMV), tristeza virus, tobacco mosaic virus (TMV), tobacco necrosis virus (TNV), beet necrotic yellow vein virus (BNYVV), rhizomania virus.

Xanthomonas species, such as, for example, *Xanthomonas campestris* pv. oryzae;

Pseudomonas species, such as, for example, *Pseudomonas syringae* pv. lachrymans;

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidial form: Drechslera, syn: Helminthosporium); Cochliobolus species, such as, for example, *Cochliobolus sativus* (conidial form: Drechslera, syn: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example;, *Cercospora canescens;*

Alternaria species, such as, for example, *Alternaria brassicae;*

Pseudocercosporella species, such as, for example, *Pseudocercosporella herpotrichoides. Helminthosporium carbonum* may also be listed.

DESCRIPTION OF THE PREFERRED EMBODIMENTS

Figure 1:
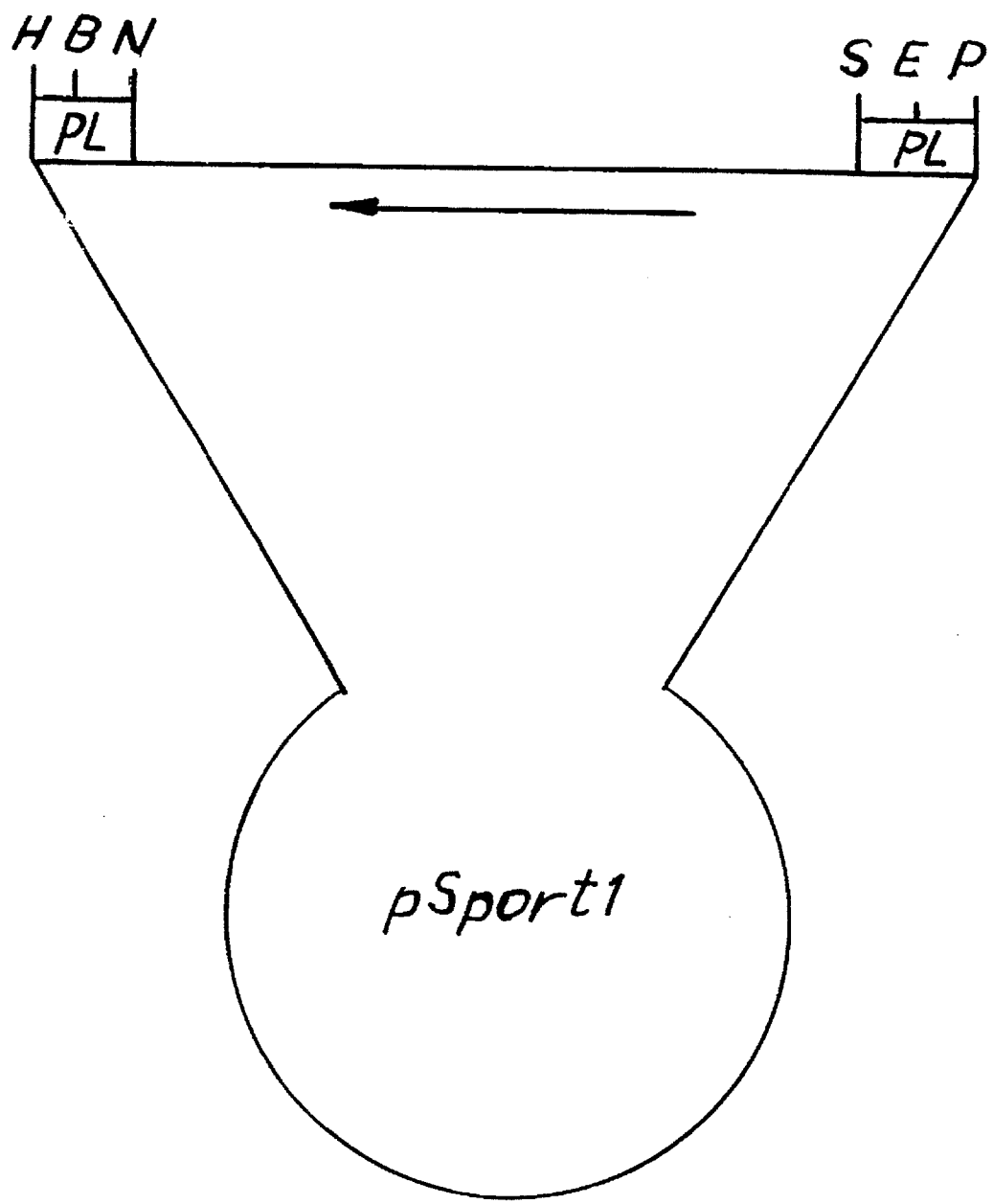
FIG. 1 is a schematic representation of the plasmid p8.1.1.

The following exemplary embodiments are intended to explain the present invention in more detail:

1. Isolation of the gene for bibenzyl synthase from orchids

Orchid plants and cell cultures contain the genes for bibenzyl synthase, which bring about the formation of bibenzyl synthase (size of the protein 90,000 D; reaction with specific antiserum). The enzyme consists of a homodimer of 43,000 D.

In isolating the bibenzyl synthase genes and the cDNA sequences, in particular the cDNA contained on the plasmid p8.1.1, use was made of the known processes and methods of molecular biology, as are, for example, described in detail in the following manual: Sambrook, J., Fritsch, E. F., Maniatis, T.: Molecular Cloning: A Laboratory Manual; Cold Spring Harbor Laboratory, Second Edition 1989.

A "gene library" is first constructed for the orchids in question: genomic DNA from enriched cell nuclei (Bedbrook, J., Plant Molecular Biology Newsletter 2, 24, 1981) is cut with the restriction enzyme NdeII such that DNA fragments are produced having an average length of approximately 12,000 nucleotide pairs. These fragments are cloned into the BamHI site of lambda phage EMBL4 (Frischauf et al., J. Mol. Biol. 170, 827–842, 1983), and the phages are replicated in E. coli. The totality of the phage polulation contains, cloned in fragments, the total genomic DNA of the orchid cells and thus the genes for bibenzyl synthases (multigen family) as well.

The genes for bibenzyl synthase, their mRNA, and the bibenzyl synthase cDNA's in each case contain equivalent nucleic acid sequences, since they can be derived from each other (gene→mRNA→cDNA). This means that the genes for bibenzyl synthase can be identified by means of specific hybridization to the respective bibenzyl synthase cDNA or to specific oligonucleotides. In accordance with this process, genomic phage clones for bibenzyl synthases are identified and transferred into tobacco, resulting in bibenzyl (1-(3,5-dihydroxyphenyl)-2-(3-hydroxyphenyl)-ethane) being produced in the heterologous plants. The transgenic plants exhibit an increased resistance to plant pathogens. The phages containing the genes are identified by hybridization and then isolated and replicated. The orchid genomic DNA cloned in these phages is then mapped by analysis with different restriction enzymes, and the position of the bibenzyl synthase genes is established by further hybridization experiments using cDNA sequences or synthetic oligonucleotides. Finally, the gene units are excised from the phage by digestion with restriction enzymes, cloned in the appropriately cut plasmid vector pUC18 (from Gibco-BRL GmbH, Eggenstein, Federal Republic of Germany), and replicated as recombinant plasmids.

2. Description of the plasmid p8.1.1 (cf. FIG. 1)

The plasmid consists of two components:

(i) Bibenzyl synthase cDNA: the cDNA, which was inserted into the plasmid pSport 1 (Gibco/BRL), is 1.6 kb in length and can be excised from plasmid p8.1.1 using MLuI.

(ii) Vector plasmid: the cDNA is cloned in the vector pSport 1 (Gibso/BRL, Eggenstein, Federal Republic of Germany). The size of the vector is 4109 nucleotide pairs. It carries the gene for ampicillin resistance, ie. E. coli cells harboring this plasmid grow in nutrient media which contain the antibiotic ampicillin. Ori: designation for sequences which are required for the replication of the plasmid in E. coli.

Plasmid p8.1.1 carries a gene for ampicillin resistance and contains, as bibenzyl synthase cDNA, the above-described MLuI fragment of about 1.6 kb. It can be replicated in a customary manner in E. coli cells which harbor p8.1.1 (E. coli p8.1.1.).

Preferred nutrient medium for E. coli cells (e.g. JA221, Nakamura, K., Inouye, M., EMBO J. 1, 771–775, 1982) which harbor p8.1.1 (E. coli pin 5-49):

| | |
|---|---|
| Bacto-peptone* | 10 g |
| Yeast extract | 5 g |
| NaCl | 5 g |
| Agar | 20 g |
| $H_2O$ | 1 l |
| pH 7.5 | |
| fermentation: 37° C., aerobic | |

(*Bacto is a trademark belonging to DIFCO Lab., Detroit, USA).

3. Transformation of tobacco a) Cultivation of tobacco shoots and isolation of tobacco protoplasts:

Nicotiana tabacum (Petit Havana SR1) is replicated as a sterile shoot culture on hormone-free LS medium (Linsmaier and Skoog 1965). Shoot segments are transferred to fresh LS medium at intervals of approximately 6–8 weeks. The shoot cultures are maintained in a culture room at 24°–26° C. with 12 h illumination (1000–3000 lux).

In order to isolate leaf protoplasts, leaves of approximately 2 g (approximately 3–5 cm in length) are cut into small pieces (0.5 cm×1 cm) using a fresh razor blade. The leaf material is incubated at room temperature for 14–16 h in 20 ml of enzyme solution, consisting of K3 medium (Nagy and Maliga 1976), 0.4 m sucrose, pH 5.6, 2% cellulase R10 (Serva) and 0.5% Macerozym R10 (Serva). After that, the protoplasts are separated from cell residues by filtration through 0.30 mm and 0.1 mm steel sieves. The filtrate is centrifuged at 100×g for 10 minutes. During the centrifugation, intact protoplasts float and collect in a band at the top of the enzyme solution. The pellet, consisting of cell residues, and the enzyme solution are sucked off using a glass capillary pipette. The prepurified protoplasts are made up to 10 ml with fresh K3 medium (0.4M sucrose as osmotic agent) and subjected to flotation once again. The washing medium is sucked off and the protoplasts are diluted to $1-2 \times 10^5$/ml for cultivation or subsequent infection with agrobacteria (coculture). The protoplast concentration is determined in a counting chamber.

b) Transformation of regenerating tobacco protoplasts by coculture with Agrobacterium tumefaciens:

In the following, the method of Marton et al. 1979 is used with slight modifications. The protoplasts are isolated as described and incubated at a density of $1-2 \times 10^5$/ml, at 26° C. and for 2 days in the dark and 1 to 2 days under weak illumination (500 lux), in K3 medium (0.4 m sucrose, 0.1 mg/1 NAA, 0.2 ml in K3 medium (0.4 m sucrose, 0.1 mg/1 NAA, 0.2 mg kinetin). 30 μl of an agrobacterium suspension in minimal A (Am) medium (density approximately $10^9$ agrobacteria/ml) are added to 3 ml of regenerating protoplasts as soon as the protoplasts are seen to be dividing. The coculture lasts for 3–4 days at 20° C. in the dark. After that, the tobacco cells are added to 12 ml centrifuge tubes, diluted to 10 ml with seawater (600 mOsm/kg) and pelleted at 60×g for 10 minutes. This washing procedure is repeated a further 1–2× in order to remove most of the agrobacteria. The cell suspension is cultivated at a density of $5 \times 10^4$/ml in K3 medium (0.3 m sucrose) containing 1 mg/l NAA (naphthyl-1-acetic acid), 0.2 mg/l kinetin and 500 mg/l of the cephalosporin antibiotic cefotaxim. The cell suspension is diluted each week with fresh K3 medium and the osmotic strength of the medium is gradually reduced by 0.05 m sucrose (approximately 60 mOsm/kg) per week. The selection with kanamycin (100 mg/l kanamycin sulfate (sigma), 660 mg/g active Km)is started in agarose "bead-type culture" (Shillito et al. 1983) 2–3 weeks after the coculture. 3–4 weeks after beginning the selection, kanamycin-resistant colonies can be distinguished from the background of retarded colonies.

c) Direct transformation of tobacco protoplasts with DNA. Calcium nitrate-PEG transformation.

Approximately $10^6$ protoplasts in 180 μl of K3 medium are mixed carefully, in a petri dish, with 20 μl of an aqueous solution of DNA which contains 0.5 μg/μl plasmid which carries the genomic bibenzyl synthase gene or a chimeric gene consisting of the stilbene synthase promoter in accordance with EP-A 0 309 862 or EP-A 0 464 461 and of the cDNA for bibenzyl synthase from p8.1.1 as well as a polyadenylation sequence, preferably from the stilbene synthase genes of EP-A 0 309 862 or EP-A 0 464 461, and 0.5 μg/μl pLGV neo 2103 (Hain et al. 1985). 200 μl of fusion solution (0.1 m calcium nitrate, 0.45M mannitol, 25% polyethylene glycol (PEG 6000), pH 9) are then added carefully. After 15 minutes, 5 ml of washing solution (0.275M calcium nitrate pH 6) are added, and, after a further 5 minutes, the protoplasts are transferred into a centrifuge tube and pelleted at 60×g. The pellet is taken up in a small quantity of K3 medium and cultured as described in the next section. Alternatively, the protoplasts can be transformed in accordance with Hain et al. 1985.

The transformation may also be carried out without adding the 0.5 μg/μl pLGV neo 2103. Since no reporter gene is employed in this case, dot blot hybridization is used to screen the resulting calluses for the presence of the bibenzyl synthase gene unit or of the chimaric gene. The cDNA sequence from p8.1.1 can be used as the hybridization probe. Naturally, other methods of detection, such as testing with antibodies or establishment of the presence of fungal resistance, may also be employed.

d) Cultivation of the protoplasts incubated with DNA and selection of kanamycin-resistant calluses:

A modified "bead-type culture" technique (Shillito et al. 1983) is used for the cultivation and the selection of kanamycin-resistant colonies described below. One week after treating the protoplasts with DNA (cf. c), 3 ml of the cell suspension are mixed in 5 cm petri dishes with 3 ml of K3 medium (0.3M sucrose+hormones; 1.2% (Seaplaque) LMT agarose (low-melting agarose, Marine Colloids). For this purpose, agarose is autoclaved in a dry state and, following the addition of K3 medium, is briefly boiled in a microwave oven. Once the agarose has set, the agarose disks ("beads") containing the embedded tobacco micro calluses are transferred into 10 cm petri dishes for further cultivation and selection and 10 ml of K3 medium (0.3M sucrose, 1 mg/l NAA, 0.2 mg/l kinetin) and 100 mg/l kanamycin sulfate (sigma) are added to each dish. The liquid medium is changed every week. In doing this, the osmotic strength of the medium is lowered step-wise.

The sucrose content of the exchange medium (K3+Km) is reduced by 0.05 m (approximately 60 mOsm) each week.

Schedule for selecting kanamycin-resistant tobacco colonies following DNA transformation:

| 0.4M U | 0.3M E S | 0.25M | 0.20M | 0.15M | 0.10M K | Sucrose in the liquid medium |
|---|---|---|---|---|---|---|
| DNA uptake | 1 | 2 | 3 | 4 | 5 | 6 Weeks after |
| | | (K3 medium 1 mg NAA, 0.2 mg kinetin) | | | | |

U=DNA uptake
E=Embedding in agarose
S=Selection with kanamycin (100 mg/l kanamycin sulfate)
K=Kanamycin-resistant colonies can be clearly distinguished from the background e) Regeneration of kanamycin-resistant plants:

As soon as the kanamycin-resistant colonies have reached a diameter of approximately 0.5 cm, half of them are placed on regeneration medium (LS medium, 2% sucrose, 0.5 mg/l benzylaminopurine BAP) and maintained in a culture room at 24° C. and at 12 h illumination (3000–5000 lux). The other half is propogated as a callus culture on LS medium containing 1 mg/l NAA, 0.2 mg/l kinetin, 0.1 mg/l BAP and 100 mg/l kanamycin sulfate. When the regenerated shoots are approximately 1 cm in size, they are cut off and placed, for rooting, on ½ LS medium (1% sucrose, 0.8% agar) without growth regulators. The shoots are rooted on ½ MS medium containing 100 mg/l kanamycin sulfate and later transferred into soil.

f) Transformation of leaf disks using Agrobacterium tumefaciens

For the transformation of leaf disks (Horsch et al. 1985), leaves, of approximately 2–3 cm in length, from sterile shoot cultures are punched into disks of approximately 1 cm in diameter, and these disks are incubated for approximately 5 minutes together with a suspension of appropriate Agrobacteria (approximately $10^9$/ml) (cf. b) in Am medium, see below). The infected leaf pieces are maintained at approximately 24° C. for 3–4 days on MS medium (see below) without hormones. During this time, the Agrobacterium overgrows the leaf pieces. The leaf pieces are subsequently washed in MS medium (0.5 mg/ml BAP, 0.1 mg/ml NAA) and laid on the same medium (0.8% agar) containing 500 μg/ml cefotaxime and 100 μg/ml kanamycin sulfate (sigma). After two weeks, the medium should be renewed. Transformed shoots become visible after a further 2–3 weeks. The shoots should be regenerated in a parallel manner, also without any selection pressure. The regenerated shoots must then be tested for transformation using biological tests, e.g. for nopaline synthase or bibenzyl synthase activity. 1–10% off transformed shoots are obtained in this way. Antibodies against bibenzyl synthase or the protein according to SEQ ID NO:2 can be obtained in a customary manner and likewise used for detecting whether transformation has occurred.

Biochemical method for detecting transformation
Detection of nopaline in plant tissues:

Nopaline is detected as described by Otten and Schilperoort (1978) and Aerts et al. (1979), as follows. 50 mg of plant material (callus or leaf pieces) are incubated at room temperature overnight in an Eppendorf tube in LS medium containing 0.1M arginine. After that, the plant material is dabbed off on absorbent paper, homogenized in a fresh Eppendorf centrifuge tube using a glass rod and centrifuged for 2 min. in an Eppendorf centrifuge. 2 μl of the supernatant are dotted onto a paper which is suitable for electrophoresis (Whatman 3 MM paper) (20×40 cm), and dried. The paper is soaked with the eluent (5% formic acid, 15% acetic acid, 80% $H_2O$, pH 1.8), and electrophoresed at 400 V for 45 minutes. Nopaline migrates towards the cathode. The paper is then dried in a hot stream of air and drawn through phenanthrenequinone staining agent (equal volumes of 0.02% phenanthrenequinone in ethanol and 10% NaOH in 60% ethanol)in the direction of migration. The dried paper is observed under long-wave UV light and photographed. The reagent stains arginine and arginine derivatives so that they fluoresce with a yellow color.

Neomycin phosphotransferase (NPT II) enzyme test:

NPT II activity is detected in plant tissue by the in-situ phosphorylation of kanamycin, as described by Reiss et al. (1984), and modified by Schreier et al. (1985), as follows. 50 mg of plant tissue are homogenized on ice in 50 μl of extraction buffer (10% glycerol, 5% 2-mercaptoethanol, 0.1% SDS, 0.025% bromophenol blue, 62.5mM Tris pH 6.8) in the presence of glass powder, and then centrifuged at 4° C. for 10 minutes in an Eppendorf centrifuge. 50 μl of the supernatant are loaded onto a native polyacrylamide gel (145×110×1.2 mm; resolving gel: 10% acrylamide, 0.33% bisacrylamide, 0.375M Tris pH 8.8, stacking gel: 5% acrylamide, 0.165% bisacrylamide, 0.125M Tris pH 6.8), and electrophoresed at 4° C. and 60 V overnight. As soon as the bromophenol blue marker runs off the gel, the latter is washed twice with distilled water for 10 min. and once with reaction buffer (67 mM Tris-maleate, pH 7.1, 42 mM $MgCl_2$, 400 mM ammonium chloride) for 30 min. The gel is laid on a glass plate of equal size and overlaid with 40 ml of a 1% solution of agarose in reaction buffer which contains the substrates kanamycin sulfate (20 μg/ml) and 20–200 μCi $^{32}P$ ATP (Amersham). The sandwich gel is incubated at room temperature for 30 min., and a sheet of phosphocellulose paper P81 (Whatman) is then laid on the agarose. Four layers of 3 MM (Whatman) filter paper, and some paper towels, are stacked on top of the phosphocellulose paper. The transfer of in-situ phosphorylated radioactive kanamycin phosphate to the P81 paper is stopped after 3–4 h. The P81 paper is incubated at 60° C. for 30 min. in a solution of proteinase K and 1% sodium dodecyl sulfate (SDS) and then washed 3–4 times, at 80° C., in 250 ml of 10 mM phosphate buffer pH 7.5, dried, and then autoradiographed (XAR5 film, Kodak) at −70° C. for 1–12 h.

4. Transformation of Solanum tuberosum (potato)

The transformation is carried out precisely in the manner indicated in EP-A-0 242 246, pages 14 to 15, with the Agrobacteria harboring Ti plasmids which carry bibenzyl synthase genes.

Unless otherwise indicated, all the percentage values in the above examples refer to percentages by weight.

In the plant cells and plants (tobacco) obtained in accordance with the above examples, the presence of the bibenzyl synthase genes is confirmed by Southern blot analysis. The expression of the bibenzyl synthase genes is determined by Northern blot analysis, and bibenzyl synthase and bibenzyl are detected using specific antibodies. Transformed and non-transformed plants (for comparison) are sprayed with a suspension of Botrytis cinera spores and the degree of fungal infestation is graded after 1 week. The transformed plants exhibited (as compared with the non-transformed plants used for comparison) an increased resistance to fungal infestation.

Hybridization to the cDNA sequence of plasmid p.8.1.1 and to the cDNA sequence in accordance with SEQ ID NO: 1

As discussed above, the preferred bibenzyl synthase genes according to the invention are characterized in that they hybridize to the cDNA sequence, or its parts, contained in the plasmid p8.1.1 or to the cDNA sequence according to SEQ ID NO: 1 or its parts, and code for bibenzyl synthase. The hybridization can also be employed, in a general manner, for determining and isolating bibenzyl synthase genes, e.g. in plants or plant parts.

Preferentially, phage clones which contain bibenzyl synthase genes can be identified by hybridization to p8.1.1 (or SEQ ID No: 1) under conditions of low stringency. A subpopulation of clones is obtained, which clones can subsequently be identified as bibenzyl synthase gene clones by, for example, direct gene transfer into plants (gain et al, 1985 and 1990) and subsequent analysis of the transgenic plant tissue for bibenzyl synthase or the protein of SEQ ID No: 2 (using antibodies), or for bibenzyl synthase enzymic activity, or for bibenzyl.

By way of example, bibenzyl synthase gene clones were identified under standard hybridization conditions using the cDNA clone p8.1.1 (or SEQ ID No: 1) as the probe. The hybridization was carried out at 68° C. for 12 hours in standard buffer containing 2 SSC. Washing took place at 74° C. in 2 SSC and 0.1% SDS (2 times 30 min.), with a subsequent washing in 0.2 SSC and 0.1% SDC (10 min.). The phage clone DNA was cotransferred with a plant-selective marker (kanamycin resistance) into tobacco protoplasts, and the bibenzyl synthase was detected in tobacco. A corresponding result was obtained by expressing the cDNA from plasmid p8.1.1 under appropriate promoters (e.g. stilbene synthase promoter according to EP-A 0 309 862 or EP-A 0 464 461).

Some of the media employed in the transformation of plants and plant cells are described below:

| Am Medium | |
|---|---|
| 3.5 g | $K_2HPO_4$ |
| 1.5 g | $KH_2PO_4$ |
| 0.5 g | $Na_3$ citrate |
| 0.1 g | $MgSO_4 \times 7H_2O$ |
| 1 g | $(NH_4)_2SO_4$ |
| 2 g | glucose |
| | to 1 l |

| Medium for the sterile culture of tobacco shoots | |
|---|---|
| Macroelements, ½ of the concentration of the MS salts | |
| Microelements, ½ of the concentration of the MS salts | |
| Fe-EDTA Murashige and Skoog (MS) | |
| Myo-Inositol | 100 mg/l |
| Sucrose | 10 mg/l |
| Agar | 8 g/l |
| Vitamins | |
| Ca panthotenate | 1 mg/l |
| Biotin | 10 mg/l |
| Nicotinic acid | 1 mg/l |
| Pyridoxine | 1 mg/l |
| Thiamine | 1 mg/l |
| pH 5.7 prior to autoclaving | |

K3Medium

For culturing Nicotiana tabacum petit Havana SR1, Nicotiana tabacum Wisconsin 38, and Nicotiana plumbaginifolia protoplasts (Nagy and Maliga, 1976)

| Macroelements | $NH_4NO_3$ | 250 mg/l |
|---|---|---|
| | $KNO_3$ | 2500 mg/l |
| | $CaCl_2.2H_2O$ | 900 mg/l |

-continued

| | | |
|---|---|---|
| | MgSO$_4$.7H$_2$O | 250 mg/l |
| | NaH$_2$PO$_4$.1H$_2$O | 150 mg/l |
| | (NH$_4$)$_2$SO$_4$ | 134 mg/l |
| | CaHPO$_4$.1H$_2$O | 50 mg/l |
| Microelements | H$_3$BO$_3$ | 3 mg/l |
| | MnSO$_4$.1H$_2$O | 10 mg/l |
| | ZnSO$_4$.4H$_2$O | 2 mg/l |
| | KI | 0.75 mg/l |
| | Na$_2$MoO$_4$.2H$_2$O | 0.25 mg/l |
| | CuSO$_4$.5H$_2$O | 0.025 mg/l |
| | CoCl$_2$.6H$_2$O | 0.025 mg/l |
| Fe-EDTA | Na$_2$EDTA | 37.2 mg/l |
| | FeSO$_4$.7H$_2$O | 27.8 mg/l |
| Inositol | | 100 mg/l |
| Sucrose | | 137 g/l (=0.4M) |
| Xylose | | 250 mg/l |
| Vitamins | Nicotinic acid | 1 mg/l |
| | Pyridoxine | 1 mg/l |
| | Thiamine | 10 mg/l |
| Hormones | NAA | 1.0 mg/l |
| | Kinetin | 0.2 mg/l |
| pH 5.6 | | |
| Sterilized by filtration | | |

Linsmaier and Skoog Medium (Linsmaier and Skoog 1965)

For culturing regenerating protoplasts and for the tissue culture of tobacco tumors and callus. Linsemaier and Skoog (LS) medium is Murashige and Skoog medium (Murashige and Skoog, 1962) with the following modifications:

Thiamine is employed at higher concentration, 0.4 mg/l instead of 0.1 mg/l;

Glycine, pyridoxine and nicotinic acid are omitted.

| | | |
|---|---|---|
| Macroelements | NH$_4$NO$_3$ | 1650 mg/l |
| | KNO$_3$ | 1900 mg/l |
| | CaCl$_2$.2H$_2$O | 440 mg/l |
| | MgSO$_4$.7H$_2$O | 370 mg/l |
| | KH$_2$PO$_4$ | 170 mg/l |
| Microelements | H$_3$BO$_3$ | 6.2 mg/l |
| | MnSO$_4$.1H$_2$O | 22.3 mg/l |
| | ZnSO$_4$.4H$_2$O | 8.6 mg/l |
| | KI | 0.83 mg/l |
| | Na$_2$MoO$_4$.2H$_2$O | 0.25 mg/l |
| | CuSO$_4$.5H$_2$O | 0.025 mg/l |
| | CoCl$_2$.6H$_2$O | 0.025 mg/l |
| Fe-EDTA | Na$_2$EDTA | 37.2 mg/l |
| | FeSO$_4$.7H$_2$O | 27.8 mg/l |
| Inositol | | 100 mg/l |
| Sucrose | | 30 g/l |
| Agar | | 8 g/l |
| Vitamins | Thiamine | 0.4 mg/l |
| Hormones: | NAA | 1 mg/l |
| | Kinetin | 0.2 mg/l |
| pH 5.7 prior to autoclaving | | |

5. Induction and purification of bibenzyl synthase from Bletilla striata 5.1 Material and methods 5.1.1 Plant material Tubers of Bletilla striata were used.

5.1.2 Solid-agar cultures of Botrytis cinerea and Rhizoctonia crocorum

The cultures were raised on potato-dextrose-agar plates (PDA plates, DIFCO Detroit, Mich. USA).

5.1.3 Induction of the bibenzyl synthase

The tubers were skinned, cut with a scalpel into slices of about 2 mm in thickness and stored at 20° C. in 100% atmospheric humidity.

For the additional treatment with fungus, 10 ml of tap water were applied to a 1 month old agar plate of Botrytis or Rhizoctonia, and mycelium (Rhizoctonia) or mycelium+ conidia (Botrytis) was brought into suspension using a spatula.

The orchid slices were immersed for 1 minute in the suspension thus obtained and then stored as described above. Having been frozen, the induced orchid slices were stored at −80° C. in liquid nitrogen.

5.1.4 Synthesis of CoA esters of substituted cinnamic and phenylpropionic acids

The CoA esters were prepared in accordance with the method described by Stöckigt and Zenk (1975), Z. Naturforsch. 30C, pages 352–358. The acid was converted into the hydroxysuccinimide ester and then transesterified to give the CoA ester. The CoA esters were purified by paper chromatography.

5.1.5 Test for bibenzyl synthase activity

The routine test was carried out using dihydro-m-coumaroyl-CoA as a substrate.

| | |
|---|---|
| Test mixture: | 5 μl of [2-$^4$C]malonyl-CoA (1.85 TBq/mol; 370 Bq/μl) |
| | 40 μl of enzyme solution |
| | 5 μl of substrate solution (1 mM) |
| Incubation: | 30 min in a 30° C. water bath |
| Test stop with: | 500 μl of double-distilled |
| | 10 μl of naringenin (1 mg/ml ethyl acetate) |

The test mixture was extracted twice by shaking on each occasion with 1 ml of ethyl acetate for 20 sec. The combined organic phases were concentrated in a vacuum centrifuge, taken up twice with 20 μl of ethyl acetate on each occasion, and loaded, as a 2.5 cm-wide strip, on a silica gel thin layer plate (containing fluorescent indicator 254 nm). Eluent: EtOAc:toluene:acetone (50:35:15 parts by volume) The radioactivity profile of the plate was recorded using a thin layer scanner (LB 2723, from Berthold). The zones containing the product were scratched out, mixed with scintillating fluid (11 eco, from Roth ), and counted.

5.1.6 Protein determination

The protein concentration was carried out using the Mikro Assay (from Bio-Rad) in accordance with a modified method of Bradford (1976) Anal. Biochem. 72, 248. BSA was used as the calibration protein.

5.1.7 Electrophoretic methods 5.1.7.1 Sample preparation

Protein was precipitated, at −20° C. and within the space of 30 min, using four times the volume of acetone, washed with 80% (v/v) acetone and 80% (v/v) ethanol, dried in a vacuum centrifuge, and dissolved in extraction medium by boiling for two minutes.

5.1.7.2 SDS-Page

The protein was fractionated in a minigel apparatus from Biometra in accordance with the method of Laemmli (1970) Nature 227, pages 680–685.

5.1.7.3 Protein staining

Coomassie staining:

The gel was tilted in staining solution for 20 min. The background was destained using destaining solution.

| | | |
|---|---|---|
| Staining solution: | Coomassie brilliant blue R 250 | 0.25% (w/v) |
| | Methanol | 50% (v/v) |
| | Glacial acetic acid | 5% (v/v) |
| Destaining solution: | Isopropanol | 40% (v/v) |
| | Glacial acetic acid | 10% (v/v) |
| Silver staining: | A method of Wray et al. (Wray, W., Boulikas, T., Wray, V.P., Hancock, R. (1981) Anal. Biochem. 118, 197–203) was used. | |

5.1.8 Chromatofocussing

The isoelectric point was determined by chromatofocussing on PBE 94. The CF was carried out using an enriched preparation of bibenzyl synthase.

5.1.8.1 Implementation

Chromatography material: PBE 94 (from Pharmacia)

Column dimensions: 1.0×22 cm; 17 ml

Equilibrated: 25 mM histidine (HCl, pH 6.2, 2 mM 2-mercaptoethanol

Elution with: Polybuffer 74-HCl (diluted 1:8 with double distilled), pH 4.0, 2 mM mercaptoethanol (starting buffer)

Flow rate: 22 ml/h

Fraction volume: 3 ml

The bibenzyl synthase was concentrated by chromatography on HAP and Sephacryl S-200 HR (see purification) and transferred into the CF starting buffer.

The peak of activity from the chromatography on S-200 (48 ml; total activity=5.4 pkat in starting buffer) at a flow rate of 12 ml/h was loaded onto the chromatofocussing column.

1.8.2 Result

| Fraction | pH |
|---|---|
| 1 | 6.2 |
| 5 | 6.2 |
| 10 | 6.1 |
| 15 | 5.8 |
| 20 | 5.6 |
| 25 | 5.3 |
| 30 | 5.0 |
| 35 | 4.8 |
| 40 | 4.5 |
| 45 | 4.2 |
| 50 | 4.0 |

| Fraction | Activity (pkat/ml) |
|---|---|
| 34 | 0.01 |
| 35 | 0.02 |
| 36 | 0.08 |
| 37 | 0.12 |
| 38 | 0.09 |
| 39 | 0.13 |
| 40 | 0.10 |
| 41 | 0.04 |
| 42 | 0.02 |

5.2 Purification of the bibenzyl synthase (from Bletilla striata)

Buffer

P1: 25 mM potassium phosphate, pH 8.0, 2 mM 2-mercaptoethanol

P2: 250 mM potassium phosphate, pH 8.0, 2 mM 2-mercaptoethanol

P3: 10 mM potassium phosphate, pH 6.4, 2 mM 2-mercaptoethanol

P4: 25 mM Tris/HCl, pH 8.0, 2 mM 2-mercaptoethanol

Column-chromatographic methods

Hydroxylapatite:

Chromatography material: Bio-Gel HTP (from Bio-Rad)

Column dimensions: 2.0×20 cm; 63 ml

Equilibrated with: P1

Linear gradient: 150 ml P1+150 ml P2

Elution flow rate: 25 ml/h

Fraction volume: 6 ml

Molecular-sieve chromatography

Chromatography material: Sephacryl S-200 HR (from Pharmacia)

Column dimensions: 2.3×105 cm; 436 ml

Equilibrated with: P3

Elution flow rate: 30 ml/h

Fraction volume: 4 ml

Affinity chromatography:

Chromatography material: Reactive Red 120-agarose, Type 3000-Cl (from Sigma)

Column dimensions: 1.1×6.0 cm; 5.7 ml

Equilibrated with: P3

Elution with: P2

Flow rate: 10 ml/h

Anion exchange chromatography (FPLC):

Column: Mono Q HR 5/5 (from Pharmacia)

Equilibrated with: P4

Linear gradient: 0–250 mM-NaCl

Elution flow rate: 1 ml/min

Fraction volume: 1 ml 80 g of induced orchid tubers were ground in a mortar under liquid nitrogen to a fine powder, to which 1000 ml of P1 and 20 g of Polyclar AT (from Serva) were added, and the whole was mixed 5×15 sec using an Ultraturrax, and centrifuged at 12,000 g for 30 min.

The viscosity of the crude extract prevented it being directly loaded onto a chromatography column. The chromatography on hydroxylapatite was therefore carried out, in part, in a batch process. The crude extract was mixed with a suspension of 20 g of HAP in 100 ml P1 and then shaken at 200 rpm for 3 h.

In order to separate off a large part of the sugars and mucilaginous substances, the HAP was centrifuged down at a low centrifugal speed (1500 g), washed three times with 500 ml of P1 on each occasion, and transferred into a column.

Elution was effected using a linear phosphate gradient of 25–250 mM. The bibenzyl synthase elutes at 160–180 mM phosphate.

The fractions possessing the highest specific activity (48 ml) were concentrated down to 15 ml in a dialysis tube using Aquacide (from Calbiochem), and loaded onto the molecular sieve.

The most active fractions (12 ml) from the Sephacryl S-200 HR chromatography were combined and loaded onto a column filled with reactive red 120-agarose (flow rate 6 ml/h).

Unbound proteins were removed using 50 ml of P3 (flow rate 80 ml/h). The elution was carried out using P2.

The activity peak of 4.5 ml was rebuffered in P4 through PD 10 (from Pharmacia) and loaded, with a flow rate of 0.5 ml/h, on Mono Q.

Elution was effected using a linear NaCl gradient of 0–250 mM in P4. The bibenzyl synthase eluted at 195–230 mM NaCl. (Fractions 10–18).

| Purification of the bibenzyl synthase from Bletilla striata | | | | |
|---|---|---|---|---|
| Fraction | Total protein (mg) | Total activity (pkat) | Specific Activity (pkat/mg) | Activity yield (%) | Concentration factor |
| Crude extract | 408.40 | 8.32 | 0.02 | 100 | 1 |
| Hydroxylapatite eluate | 17.18 | 6.86 | 0.40 | 82 | 20 |
| Sephacryl S200 HR-eluate | 2.24 | 5.74 | 2.56 | 69 | 128 |
| Red agarose eluate | 1.16 | 3.58 | 3.09 | 43 | 155 |
| Mono Q eluate | 0.11 | 0.50 | 4.55 | 6 | 228 |

The following literature can be cited in relation to the topic "bibenzyls:

Gäumann, E. and Kern, H. (1959) Phytopathol. Z. 36,1.

Arditti, J. (1979) Adv. Bot. Res. 7, 421.

Stoessl, A. (1982) in Phytoalexins (Bailey, J. A. and Mansfield, J. W., eds.) p. 133, Blackie, Glasgow.

Majumder, P., Laha, S. and Datta, N. (1982) Phytochem. 21, 478.

Majumder, P. L. and Sen, R. C. (1987) Phytochem. 26, 2121.

Majumder, P. L. and Chatterjee, S. (1989) Phytochem. 28, 1986.

The following literature can be cited with regard to the transformation of plants and plant cells:

Aerts M, Jacobs M, Hernalsteens JP, Van Montagu M, Schell J (1983) Induction and in vitro culture of Arabidopsis thaliana crown gall tumours. Plant Sci Lett. 17:43–50

Fromm ME, Taylor LP, Walbot V (1986) Stable transformation of maize after gene transfer by electroporation. Nature 319: 791–793

Hain, R., Stabel, P., Czernilofsky, A.Pp., Steinbiss, H. H., Herrera-Estrella, L., Schell, J. (1985) Uptake, integration, expression and genetic transmission of a selectable chimeric gene by plant protoplasts. Molec Gen Genet 199: 161–168

Herrera-Estrella L., De Block M., Messens E., Hernalsteens JP., van Montagu M., Schell J. (1983) EMBO J. 2: 987–995.

Horsch RB, Fry JE, Hoffmann NL, Eichholtz D, Rogers SG, Fraley RT (1985) A simple and general method for transferring genes into plants. Science 277: 1229–1231

Krens FH, Molendijk L, Wullems GJ, Schilperoort RA (1982) in vitro transformation of plant protoplasts with Ti-plasmid DNA. Nature 296: 72–74

Koncz C, Schell J (1986) The promotor of $T_L$-DNA gene 5 controls the tissue-specific expression of chimaeric genes carried by a novel type of Agrobacterium binary vector. Mol. Gen. Genet. (1986) 204:338–396

Linsmaier DM, Skoog F (1965) Organic growth factor requirements of tobacco tissue cultures. Physiol Plant 18:100–127

Marton L, Wullems GJ, Molendijk L, Schilperoort PR (1979) In vitro transformation of cultured cells from Nicotiana tabacum by Agrobacterium tumefaciens. Nature 277: 1229–131

Murashige, T. and Skoog F. (1962) A revised medium for rapid growth and bioassay with tobacco tissue culture. Physiol. Plant. 15, 47

Nagy JI, Maliga P (1976) Callus induction and plant regeneration from mesophyll protoplasts of Nicotiana sylvestris. Z Pflanzenphysiol 78:453–455

Otten LABM, Schilperoort RA (1978) A rapid microscale method for the detection of Lysopin and Nopalin dehydrogenase activities. Biochim biophys acta 527:497–500

Paszkowski J, Shillito RD, Saul M, Mandak V, Hohn T, Hohn B, Potrykus I (1984) Direct gene transfer to plants. EMBO J 3:2717–2722

Shillito RD, Paszkowski J. Potrykus I (1983) Agarose plating and Bead type culture technique enable and stimulate development of protoplast-derived colonies in an number of plant species. Pl Cell Rep 2:244–247

Van den Elzen PJM, Townsend J, Lee KY, Bedbrook JR (1985) Achimaeric resistance gene as a selectable marker in plant cells. Plant Mol. Biol. 5, 299–302.

Van Haute E, Joos H, Maes M, Warren G, Van Montagu M, Schell J (1983) Intergenic transfer and exchange recombination of restriction fragments cloned in pBR322; a novel strategy for the reversed genetics of Ti plasmids of /Agrobacterium tumefaciens. EMBO J 2:411–418

Velten J, Velten L, gain R, Schell J (1984) Isolation of a dual plant promotor fragment from the Ti Plasmid of Agrobacterium tumefaciens. EMBO J 12:2723–2730

Wullems GJ, Molendijk L, Ooms G, Schilperoort RA (1981) Differential expression of crown gall tumor markers in transformants obtained after in vitro Agrobacterium tumefaciens—induced transformation of cell wall regenerating protoplasts derived from Nicotiana tabacum. Proc Natl Acad Sci 78:4344–4348

Zambryski P, Joos H, Genetello C, van Montagu M, Schell J (1983) Ti-plasmid vector for the introduction of DNA into plant cells without altering their normal regeneration capacity, EMBO J 12: 2143–2150.

Reiss B, Sprengel R, Will H and Schaller H (1984) A new sensitive method for qualitative and quantitative assay of neomycin phosphotransferase in crude cell tracts, GENE 1081:211–217

Schreier P, Seftor E, Schell J and Bohnert H (1985) The use of nuclear-encoded sequences to direct the light-regulated synthesis and transport of a foreign protein into plant chloroplasts, EMBO J Vol. 4, No. 1:25–32

In addition, the following published patent applications can be cited:

EP-A 116 718

EP-A 159 418

EP-A 120 515

EP-A 120 516

EP-A 172 112
EP-A 140 556
EP-A 174 166
EP-A 122 791
EP-A 126 546
EP-A 164 597
EP-A 175 966
WO 84/02913
WO 84/02919
WO 84/02920
WO 83/01176

Explanation of FIG. 1

FIG. 1 represents the plasmid p8.1.1. The bibenzyl synthase cDNA is located on the Mlu I fragment of approximately 1.6 kb in size.

The meanings of the abbreviations in FIG. 1 are as follows:

| E: | EcoRI | S: | Sal I |
| B: | Bam HI | P: | Pst I |
| H: | Hind III | N: | Not I |
| PL: | polylinker from the plasmid pSport 1 | | |

---

We claim:

1. An isolated and purified DNA sequence comprising a nucleotide sequence that encodes a bibenzyl synthase isolatable from an orchid.

2. Isolated and purified DNA according to claim 1, which hybridizes under conditions of low stringency to the bibenzyl synthase cDNA sequence contained in plasmid p8.1.1 or to the cDNA sequence of SEQ ID NO: 1.

3. Isolated and purified DNA sequence according to claim 1, encoding a bibenzyl synthase from Phalaenopsis spp., *Bletilla striata* or *Epipactis palustris*.

4. A vector DNA or an isolated genomic procaryotic or eucaryotic DNA, which comprises a DNA sequence according to claim 1.

5. A vector comprising a DNA sequence according to claim 1.

6. A vector according to claim 5, which is the plasmid p8.1.1.

7. A transformed microorganism comprising a plasmid which comprises a DNA sequence according to claim 1.

8. A transformed microorganism according to claim 7, which is *Escherichia coli* strain E. coli p8.1.1 or a mutant of said strain comprising plasmid p8.1.1.

9. Transgenic plant cells comprising a DNA sequence according to claim 1 as foreign DNA or additional DNA.

10. Transgenic plant cells according to claim 9, which are protoplasts.

11. Transgenic whole plants comprising a DNA sequence according to claim 1 as foreign DNA or additional DNA.

12. Transgenic parts of plants comprising a DNA sequence according to claim 1 as foreign DNA or additional DNA.

13. Transgenic plant seeds comprising a DNA sequence according to claim 1 as foreign DNA or additional DNA.

14. Propagation material obtained by propagating transgenic plant cells according to claim 9.

15. Propagation material obtained by propagating transgenic whole plants according to claim 11.

16. Propagation material obtained by propagating transgenic parts of plants according to claim 12.

17. Propagation material obtained by propagating transgenic plant seeds according to claim 13.

18. The cDNA of SEQ ID NO: 1.

19. A process for isolating a DNA sequence encoding a bibenzyl synthase from an orchid comprising the steps of:

(i) isolating total DNA from said orchid;

(ii) cleaving said total DNA into fragments with a restriction endonuclease;

(iii) cloning said fragments into vectors; and (iv) identifying a DNA sequence encoding a bibenzyl synthase by a process comprising hybridizing said vectors under conditions of low stringency with a probe comprising the cDNA according to claim 18.

20. An isolated and purified DNA sequence according to claim 1, which comprises a nucleotide sequence that encodes the bibenzyl synthase encoded by the nucleotide sequence of SEQ ID NO: 1.

21. A transformed plant cell, said plant cell comprising in its genome a DNA sequence in addition to the DNA naturally constituting the genome of said plant cell, said DNA sequence consisting of a DNA sequence according to claim 20, wherein said DNA sequence is expressed when said plant cell is exposed to a plant fungi, said plant cell having increased resistance to said plant fungi as compared to an untransformed plant cell of the same plant species and cell type exposed to the same plant fungi under the same conditions, and said increased resistance to said plant fungi being a result of the expression of said DNA sequence.

22. A transformed plant cell according to claim 21, which is a protoplast.

23. A transformed whole plant, said whole plant comprising in its genome a DNA sequence in addition to the DNA naturally constituting the genome of said whole plant, said DNA sequence consisting of a DNA sequence according to claim 20, wherein said DNA sequence is expressed when said whole plant is exposed to a plant fungi, said whole plant having increased resistance to said plant fungi as compared to an untransformed whole plant of the same plant species exposed to the same plant fungi under the same conditions, and said increased resistance to said plant fungi being a result of the expression of said DNA sequence.

24. A transformed plant part, said plant part comprising in its genome a DNA sequence in addition to the DNA naturally constituting the genome of said plant part, said DNA sequence consisting of a DNA sequence according to claim 20, wherein said DNA sequence is expressed when said plant part is exposed to a plant fungi, said plant part having increased resistance to said plant fungi as compared to an untransformed plant part of the same plant species and plan, part type exposed to the same plant fungi under the same conditions, and said increased resistance to said plant fungi being a result of the expression of said DNA sequence.

25. A transformed plant seed, said plant seed comprising in its genome a DNA sequence in addition to the DNA naturally constituting the genome of said plant seed, said DNA sequence consisting of a DNA sequence according to claim 20, wherein said DNA sequence is expressed when said plant seed is exposed to a plant fungi, said plant seed having increased resistance to said plant fungi as compared to an untransformed plant seed of the same plant species exposed to the same plant fungi under the same conditions, and said increased resistance to said plant fungi being a result of the expression of said DNA sequence.

* * * * *

UNITED STATES PATENT AND TRADEMARK OFFICE
CERTIFICATE OF CORRECTION

PATENT NO. : 5,589,620
DATED : December 31, 1996
INVENTOR(S) : Kindl, et al.

It is certified that error appears in the above-indentified patent and that said Letters Patent is hereby corrected as shown below:

Col. 23, line 49   After " DNA " insert -- sequence --

Col. 26, line 14   Delete " plan " and substitute -- plant --

Signed and Sealed this

First Day of July, 1997

Attest:

BRUCE LEHMAN

Attesting Officer    Commissioner of Patents and Trademarks